United States Patent
Tivig et al.

(10) Patent No.: US 10,650,915 B2
(45) Date of Patent: May 12, 2020

(54) CLINICIAN DECISION SUPPORT SYSTEM

(75) Inventors: Gerhard Tivig, Boeblingen (DE);
Sebastian Hebler, Herrenberg (DE);
Oliver Roth, Herrenberg (DE); Erica Cummings, Wendlingen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1764 days.

(21) Appl. No.: 12/445,366

(22) PCT Filed: Oct. 8, 2007

(86) PCT No.: PCT/IB2007/054082
§ 371 (c)(1),
(2), (4) Date: Apr. 13, 2009

(87) PCT Pub. No.: WO2008/044189
PCT Pub. Date: Apr. 17, 2008

(65) Prior Publication Data
US 2010/0010319 A1    Jan. 14, 2010

(30) Foreign Application Priority Data
Oct. 12, 2016  (EP) .................................. 06122149

(51) Int. Cl.
*G16H 10/20*    (2018.01)
*G06F 19/00*    (2018.01)

(52) U.S. Cl.
CPC ......... *G16H 10/20* (2018.01); *G06F 19/3481* (2013.01)

(58) Field of Classification Search
CPC ....... A61B 5/022; A61B 5/02455; A61B 5/08; A61B 5/14551; A61B 5/412; A61B 5/6826; A61B 5/6838; A61B 5/082; A61M 5/1723

USPC ................................... 600/300–301; 705/2–4
See application file for complete search history.

(56) References Cited

U.S. PATENT DOCUMENTS

| | | | |
|---|---|---|---|
| 5,255,187 A * | 10/1993 | Sorensen | ...................... 600/300 |
| 5,781,442 A | 7/1998 | Engleson et al. | |
| 5,823,949 A | 10/1998 | Goltra | |
| 6,037,940 A | 3/2000 | Schroeder et al. | |
| 6,725,447 B1 | 4/2004 | Gilman et al. | |

(Continued)

FOREIGN PATENT DOCUMENTS

| | | | |
|---|---|---|---|
| JP | H11505352 A | 5/1999 | |
| JP | 2002203045 A | 7/2002 | |

(Continued)

OTHER PUBLICATIONS

H. Bryant Nguyen, "The STOP Sepsis Bundle Toolkit", Sep. 2006, Loma Linda University, Version 9.3 pp. 1-24 www.llu.edu/llumc/emergency/patientcare.*

*Primary Examiner* — Boniface N Nganga (57) ABSTRACT

A bedside patient monitor comprises a clinician support system. The clinician support system comprises at least one of the following modules of: a disease-specified decision module (11), disease-specified treatment module (13) or disease-specified observation module (15). The bedside monitor comprises a first interface (105) for manual patient-related input and a second interface (107) for continuous input of a sensor signal. The clinician is supported to deliver requested information and execute the treatment in a pre-determined way supported by the clinician support system.

18 Claims, 9 Drawing Sheets

(56) References Cited

U.S. PATENT DOCUMENTS

| | | | |
|---|---|---|---|
| 7,798,961 B1* | 9/2010 | Bakhshandeh | 600/300 |
| 2002/0195488 A1* | 12/2002 | Walsh | A61N 5/1048 235/380 |
| 2003/0014279 A1 | 1/2003 | Roman et al. | |
| 2004/0015337 A1* | 1/2004 | Thomas et al. | 703/11 |
| 2004/0044546 A1 | 3/2004 | Moore | |
| 2004/0078211 A1* | 4/2004 | Schramm-Apple et al. | 705/1 |
| 2004/0078231 A1* | 4/2004 | Wilkes et al. | 705/2 |
| 2004/0122708 A1* | 6/2004 | Avinash et al. | 705/2 |
| 2004/0167804 A1* | 8/2004 | Simpson | A61B 5/0002 705/3 |
| 2004/0172305 A1* | 9/2004 | Soerensen et al. | 705/3 |
| 2004/0181115 A1* | 9/2004 | Sandyk | A61N 1/40 600/9 |
| 2004/0230458 A1 | 11/2004 | Takayama et al. | |
| 2004/0260666 A1* | 12/2004 | Pestotnik et al. | 706/46 |
| 2005/0125256 A1* | 6/2005 | Schoenberg et al. | 705/2 |
| 2005/0177400 A1* | 8/2005 | Rosenfeld et al. | 705/3 |
| 2005/0234740 A1* | 10/2005 | Krishnan et al. | 705/2 |
| 2006/0025657 A1* | 2/2006 | Rosenfeld et al. | 600/300 |
| 2006/0031094 A1 | 2/2006 | Cohen et al. | |
| 2006/0111933 A1* | 5/2006 | Wheeler | 705/2 |
| 2006/0122869 A9 | 6/2006 | Rosenfeld et al. | |
| 2006/0135859 A1 | 6/2006 | Iliff | |
| 2006/0173715 A1* | 8/2006 | Wang | 705/2 |
| 2006/0271407 A1* | 11/2006 | Rosenfeld et al. | 705/3 |
| 2006/0271409 A1* | 11/2006 | Rosenfeld et al. | 705/3 |
| 2007/0005397 A1* | 1/2007 | Lee | G06F 19/322 705/3 |
| 2007/0088572 A1* | 4/2007 | Susai et al. | 705/2 |
| 2007/0168223 A1* | 7/2007 | Fors et al. | 705/2 |
| 2007/0176931 A1* | 8/2007 | Tivig et al. | 345/440 |
| 2008/0208618 A1* | 8/2008 | Schoenberg | G06F 19/322 705/2 |

FOREIGN PATENT DOCUMENTS

| | | |
|---|---|---|
| JP | 2004280807 A | 10/2004 |
| WO | 2006035383 A1 | 4/2006 |

* cited by examiner

| Clinician support system - Sepsis decision module | | X |
|---|---|---|
| Which of the following signs and symptoms of infection are both present and new to the patient? | | |
| T<36.0°C (96.8°F) or T>38.3°C (100.9°F) | 36.7°C | ▦ |
| Tachycardia (HR>90bpm) | 60bpm | ▦ |
| Tachypnea (RR>20rpm) or mechanically ventilated | 20 rpm | ☐ |
| WBC >12000/ml or <4000/ml or >10% immature forms | | ☐ |
| Acutely altered mental status | | ☐ |
| Chills with rigors | | ☐ |
| Hyperglycemia (Glucose>120mg/dl) | | ☐ |

FIG. 4

| Sepsis decision module | | | X |
|---|---|---|---|
| Is the patient history suggestive of a new infection | | | |
| | | | |
| Show Details | | Yes | No |

| Sepsis decision module | X |
|---|---|
| SSC guideline recommends measuring Lactate now. | |
| Lactate>4mmol/l (36mg/dl) ? | ☐ |

| | | |
|---|---|---|
| Enter Lact | | Confirm |

| Sepsis decision module | | | X |
|---|---|---|---|
| Does the patient have persistent Hypotension | | | |
| | | | |
| Show Details | | Yes | No |

Sepsis decision module [X]

Is the previously acknowledged infection still present?

| Show Details | | Yes | No |
|---|---|---|---|

Sepsis decision module [X]

The patient meets the SSC guideline criteria for Sepsis. Review by authorized clinician is recommended. [✓]

| Protocol Log | | Confirm |
|---|---|---|

| Sepsis treatment module | X |
|---|---|
| These are the SSC recomendations for the treatment process (6 hours): | |
| Measure Serum Lactate | ▓ |
| Take Blood Cultures | ☐ |
| Administer Intravenous Antibiotics | ☐ |
| Maintain MAP > 65mmHg (9.0kPa) | ▓ |
| Achieve $ScvO_2$ >70% ($SvO_2$ >65%) | ▓ |
| Achieve CVF > 8mmHg (1.0kPa) | ☑ |

| Show Details | Enter $ScvO_2$ | Enter Lact | | Confirm |
|---|---|---|---|---|

FIG. 11

| | Sepsis treatment module | | | | X |
|---|---|---|---|---|---|
| | All SSC recommendations have been fulfilled. Proceed with the observation process ? | | | | |

| | | | | | | |
|---|---|---|---|---|---|---|
| | Enter ScvO$_2$ | Enter Lact | | | Yes | No |

FIG. 12

| | Sepsis observation module | X |
|---|---|---|
| | All SSC guideline recommendations have to be fulfilled during the Management Bundle : | |
| | Low Dose Steroids per policy | ☐ |
| | Drotrecogin Alfa per policy | ☐ |
| | Maintain Glucose < 150 mg/dl (8.3mmol/l) | ▧ |
| | Maintain Insp. Plateau Pressure < 30 cmH$_2$O | ▧ |

| | | |
|---|---|---|
| Show Details | | Confirm |

FIG. 13

| | |
|---|---|
| No Patient Admitted | |
| SSC Sepsis | 31 May 06 10:51:56 |

31 May 2006 10:50
Log Start

31 May 2006 10:50
Start "Sepsis decision module"

31 May 2006 10:50
Action Required
   Which of the following signs and symptoms of infection are both present and new to the patient?

31 May 2006 10:51
Which of the following signs and symptoms of infection are both present and new to the patient?
   T<36°C (96.8°F) or T>38.3°C (100.9°F) ☐
   Tachycardia (HR>90bpm) ☐
   Tachypnea (RR>20rpm) or mechanically ventilated ☑
   WBC >12000/µl or <4000/µl or >10% immature forms ☑
   Acutely altered mental status ☐
   Chills with rigors ☐
   Hyperglycemia (Glucose>120mg/dl) ☐

31 May 2006 10:51
Action Required
   Is the patient history suggestive of a new infection?

31 May 2006 10:51
Is the patient history suggestive of a new infection? ☑

31 May 2006 10:51
Action Required
   SSC guideline recommends measuring Lactate now.

31 May 2006 10:51
Lact = 4.5 mmol/l (31 may 10:51)

31 May 2006 10:51
Action Required
   The patient meets the SSC guideline criteria for Sepsis. Review by authorized clinician is recommended.

31 May 2006 10:51
The patient meets the SSC guideline criteria for ☑
   Sepsis. Review by authorized clinician is recommended.

31 May 2006 10:51
Start "Sepsis treatment module"

FIG. 14

CLINICIAN DECISION SUPPORT SYSTEM

This invention is directed to a clinician decision support system.

US 2006/0122869 A9 discloses a system and method for standardizing care in a hospital environment from a remote location. The information concerning the latest care and practice standards for a given condition is provided to a decision support module. The decision support module comprises decision support algorithms that reflect a standardized guideline of practice for a particular medical condition. By means of this system it is possible to provide a 24-hours/7-days-a-week patient monitoring and management service to multiple, geographically dispersed Intensive Care Units. To allow remote visual monitoring of the patients, the system comprises video monitors. The system comprises an interface to allow a physician to get access to a physician resource database. The database comprises diagnosis algorithms. So the physician gets standardized information about a standardized diagnosis algorithm. Further standardized care and treatment is provided by the physician resource database.

Many medical organizations are active in developing guidelines for recognition of a disease and treatment of the disease, for example "surviving sepsis campaign".

It is an object of the invention to provide a support device/system to support the medical staff in the use of standardized guidelines and standardized treatment guidelines.

This object is achieved by means of a clinician support system. The clinician support system comprises at least one of the following modules: a disease-specified decision module, disease-specified treatment module or disease-specified observation module and a first interface for manual patient-related input and a second interface for continuous input of sensor signals. So it is possible to deliver manually measured physiological values by means of the first interface. Further, continuously measured signals are delivered by the second interface. Continuously measured signals are signals measured within predetermined time intervals, and the measured signals will be delivered automatically, without user interaction.

In one embodiment of the bedside patient monitor of the invention, the clinician support system comprises at least one disease-specified treatment module to support the clinician in the treatment process, the disease-specified treatment module being started only by a qualified manual input trigger signal.

In one embodiment of the bedside patient monitor, the clinician support system comprises at least one observation support module for observation of the treated patient and the disease-specified observation module is activated by a signal generated through deactivation of the disease-specified treatment module.

In a further embodiment of the bedside patient monitor, an indicator is provided for signaling a running treatment procedure. So it could be recognized instantly that a treatment procedure is running. This helps the clinician's staff in planning further action for the patient. Further, if a clinician support screen is displayed on the display of the bedside patient monitor the clinician is supported in getting a good overview of the status of the patient. For example the indicator of the running disease-specified module. The icon can be used for indication of the actual running module, if a decision, treatment or observation module is running. Different icons can be used for different diseases.

In one embodiment of the bedside patient monitor, the clinician support system comprises an information delivery tool. The information delivery tool spreads around a request for information in the case that the requested information is not delivered by the second interface. For example a request is sent to the central station of the hospital, using a network connection, especially wireless connection, to the hospital network or a request is delivered to a remote microbiological institute or center by means of the internet. The request comprises a patient identification to make sure that the information assigned to the correct patient will be delivered. For example, an identification code is provided by a bedside device, for example the bedside patient monitor.

Especially body fluids or probes are analyzed in remote microbiological centers. So this requested information, if available, is delivered to the clinician support system. Of course the request could comprise patient identification information to make sure that the requested information of the correct patient will be delivered. If the requested information is not available, the information delivery tool generates a pop-up window on the display of the bedside patient monitor to trigger manual input through the first interface. The pop-up window will disappear if the requested information is delivered.

The bedside patient monitor is used to carry out the clinician support method. During the clinician support method at least one of disease-specified modules to support the decision process, treatment process or observation process are activated. The method comprises the recognition of automatic input and the triggering of manual input to provide the information requested by a running module.

In one embodiment, the method generates pop-up windows, to trigger the manual input. The pop-up windows are displayed on the display of the patient monitor. In dependence on the requested input, the manual input of different persons will be accepted. For example a manual input of a temperature measurement value carried out by the patient himself could be accepted.

In one embodiment the method stores the manual input information linked with an identification code. The identification code is assigned to a person or a group of persons. By means of this identification code it is possible to establish which person made the manual input.

In one embodiment a method is provided, wherein the request for manual input requested by a running treatment process is carried out preferred to a request of a running decision or running observation module.

In a further embodiment a request generated by a running decision module is carried out preferred to a generated request of a running observation module.

In one embodiment an unanswered request will appear after a predetermined time. Especially 5, 10 or 15 minutes after closure of the request window, the request will reappear. Especially in dependence on the requested information, different durations for reappearance of the window can be predetermined.

In the following, the clinician support system and method of clinician support is described in more detail. A very detailed description is given in respect of the disease of sepsis, but the scope of this invention is not limited to the described specific embodiments.

The clinician support system supports the clinical staff in recognition, treatment and observation of several diseases. There are many activities in the medical society to generate standardized guidelines for treatment of several diseases, for example sepsis.

The invention is described in more detail hereinafter, especially for the example of sepsis.

FIG. 14: Protocol Log Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Figure 1:
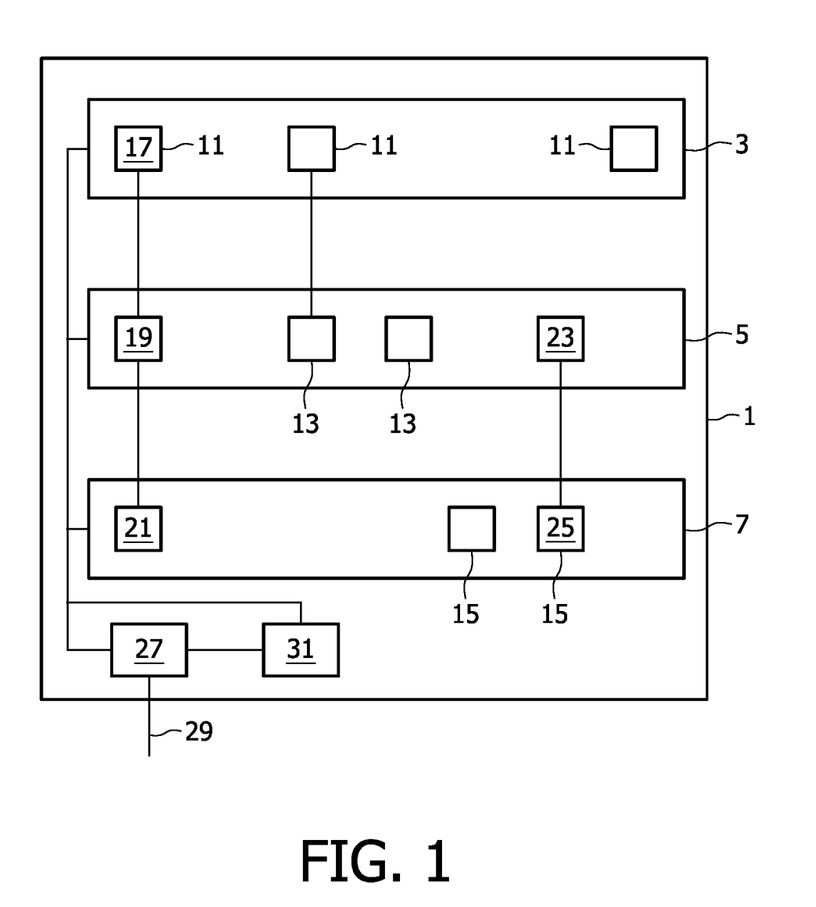
FIG. 1: Clinician support system

In FIG. 1 the general structure of the clinician support system 1 is shown. The clinician support system comprises a decision support module 3 comprising disease-specified decision modules 11. Here a disease-specified module is a sepsis decision module 17. The sepsis decision module is linked with a sepsis treatment module 19. The sepsis treatment module is one example of a disease-specified treatment module 13. The disease-specified treatment modules 13 are part of a treatment support module 5. Disease-specified observation modules 21 are part of an observation support module 7.

Disease-specified observation modules 15 are part of an observation support module 7. A disease-specified observation module 15 could be assigned to a disease-specified treatment module 13. As shown in FIG. 1, an treatment, decision and observation modules are not provided for all diseases. The modules 11, 13, 15 assigned to the same disease are linked. So the sepsis decision module is linked with the sepsis treatment module. A sepsis treatment module 21 is linked with the sepsis observation module. In the same way, the weaning treatment module 23 is linked with the weaning observation module 25. It is also possible to use the clinician support system only for the decision process 4 or the treatment process 6 or the observation process 8.

The decision support module 3, treatment support module 5, observation support module 7 are linked to an information delivery tool 27. A further storage 31 to store patient related information and to store guidelines supported by the clinician support module such as the Sepsis Resuscitation Bundle, is provided.

In the following the invention is described for the disease of sepsis/septic shock in more detail. Of course the use of the clinician support system is not limited to this example.

The clinician support system 1 comprises decision support module 3, treatment support module 5 and observation support module 7.

The decision support module 3 comprises the sepsis decision module 17. The sepsis decision module 17 provides support in respect of measurement values and evaluation of the patient status compared to the standardized sepsis guidelines criteria.

The surviving sepsis campaign (SSC) developed a guideline for detection, treatment and observation of septic patients. The clinician support system 1 supports the clinician in using for example the surviving sepsis campaign (SSC) guidelines. The clinician support system 1 assists in recognizing the early signs and symptoms of the specified diseases, for example sepsis, by comparing the detected state of the patient to the guidelines criteria. After recognition of this specific disease, the clinician is guided through the recommended treatment steps as defined in the guideline by the treatment support module 5 comprising disease-specified treatment module 13, here sepsis treatment module 19.

When the sepsis decision module 17 has recognized that the specified criteria have been met, the sepsis decision module 17 triggers to display of a predetermined window. This window requests a confirmation of the presence of infection and sepsis-related organ dysfunction by a qualified person. It is possible to display the window for this request only on a bedside patient monitor 101 assigned to that patient to make sure that the qualified person gets an impression of the acuteness.

The sepsis treatment module 19 is activated by a qualified trigger signal generated through the manual input 105 of the bedside patient monitor. Only a professional clinician is qualified to generate the qualified manual input trigger signal. The recognition of a manual input trigger signal generated by a qualified person could be approved by a requested identification code, fingerprint and so on.

The treatment support module 5 supports the treatment of the patient in general, said treatment support module comprises disease-specified treatment modules 13 to provide support in the treatment of a special disease. So to carry out the sepsis treatment guideline named Sepsis Resuscitation Bundle is supported by the sepsis treatment module 19.

The sepsis treatment module triggers the display of the surviving sepsis campaign (SSC) recommendations listings for resuscitation on the display of the bedside patient monitor.

The recommendations can be checked off as they are implemented. After the sepsis treatment module 19 recognizes the achievement of all the resuscitation goals, or after 6 hours at the latest, the sepsis treatment module 19 is completed and the sepsis observation module 21 is activated by a trigger signal generated by the treatment support module 19.

Figure 2:
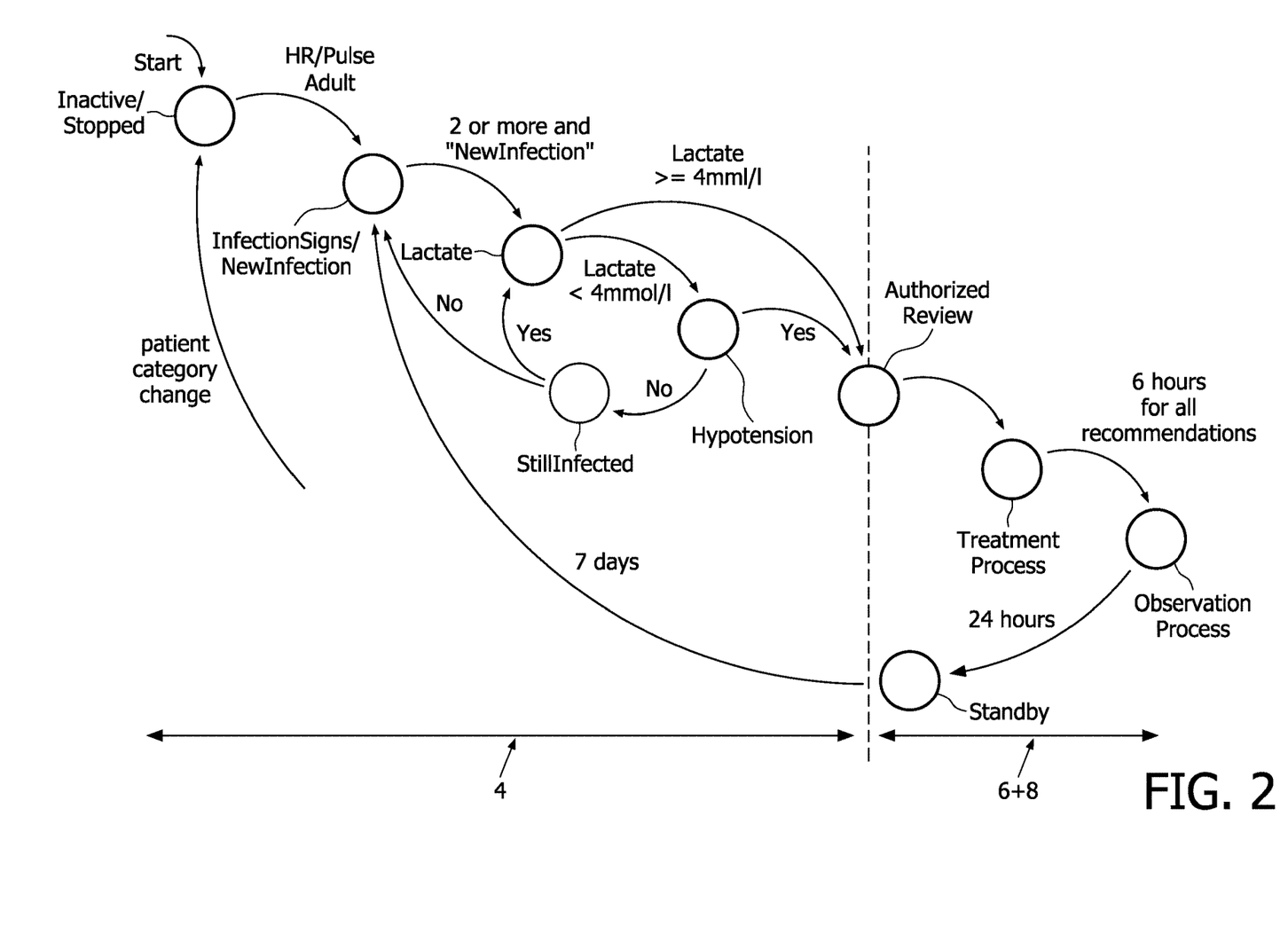
FIG. 2: Bedside patient monitor comprising the clinician support system

The sepsis observation module 21 supports the clinician to carry out the Sepsis Management Bundle—the SSC recommendations to maintain patient status are listed and can be checked off as they are implemented. The Sepsis Management Bundle ends when 24 hours have passed since the Sepsis Resuscitation Bundle began, or if all recommendations of the Management Bundle were checked off, FIG. 2. If a patient has already been diagnosed as septic before connecting him to the monitor, the septic treatment module can be activated/entered by a qualified manually generated trigger signal.

Figure 3:
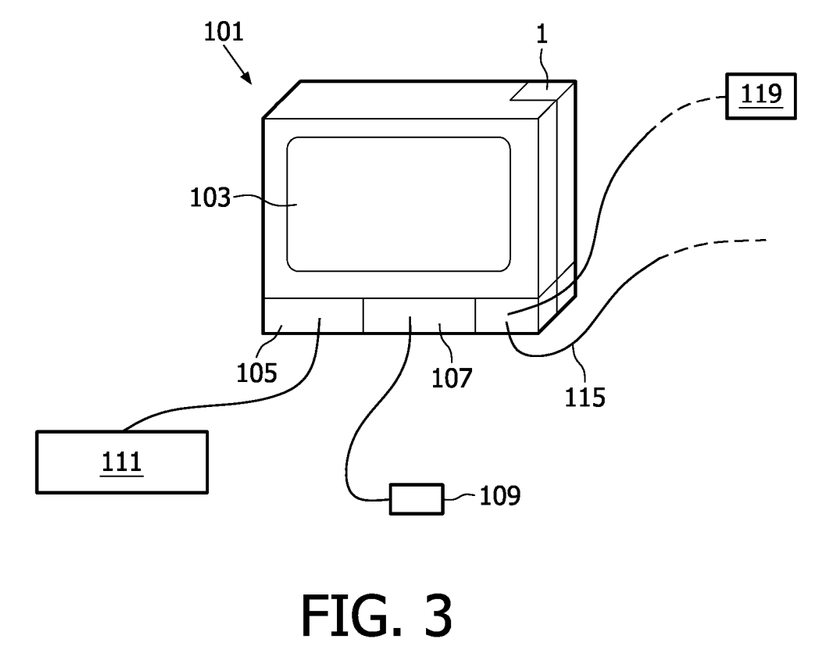
FIG. 3: Flowchart of sepsis decision, treatment and observation process

In FIG. 3 a bedside patient monitor 101 comprising a clinician support module 1 is shown. The bedside patient monitor 101 comprises a first interface 105 connected to a keyboard 111 and a second interface 107 connected to at least one patient-connected device or sensor. The patient-connected device is used for providing physiological information automatically, for example continuous temperature measurements. The bedside patient monitor comprises a display 103. The bedside patient monitor comprises the option to establish a connection to a clinical network 115 and/or the Internet. The network connection can be a wireless connection. The Internet connection can be used to update stored clinician recommendations and guidelines on a regular basis automatically. Further, the Internet or clinician network connection can be used to provide patient-related information generated for example at a microbiological laboratory, which could be separate from the hospital.

If a disease-specific predetermined set of information is recognized by the clinician support system 1, the disease-specific decision support module 11 is started. In the case of sepsis the sepsis decision module 17 is started as soon as an adult patient is connected to the bedside patient monitor, and heart rate or pulse is being measured. The sepsis decision module 17 triggers to observe heart rate, temperature and respiration rate values in the background. If temperature information or respiration rate information is not measured continuously by way of a sensor 108 connected to a second interface 107 for continuous measurement, a pop-up window will appear at predetermined intervals, for example 4-hour intervals, to trigger the manual measurement and input of the requested information. The information will be delivered to the sepsis decision module by use of the first interface 105 for manual input. The pop-up window can be closed without entering the requested information, but after a predetermined interval, preferably shorter than the normal interval, pop up of this window is triggered again by the sepsis decision module 17.

The manually entered values are labeled with the information about the person and time of input. These available values are all compared to the sepsis guideline criteria: HR above 90, Temp above 38.3° C. (100.9° F.) or below 36.0° C. (96.8° F.), respiration rate (RR) above 20.

Figure 4:
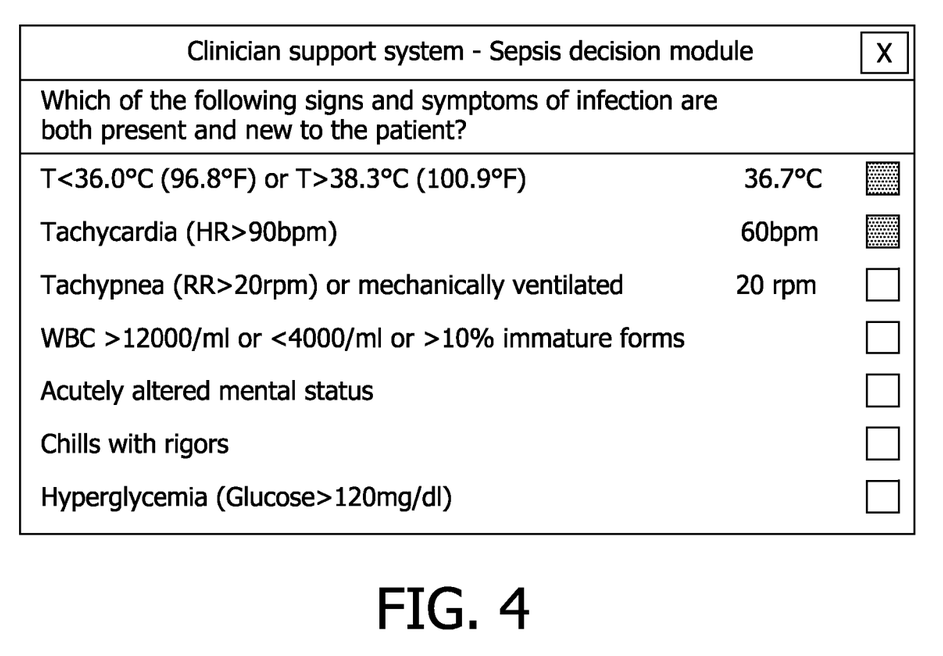
FIG. 4: Infection Signs und Symptoms window

If any one of the values fulfils the screening criteria, the sepsis decision module 17 triggers display of an Infection Signs and Symptoms window shown in FIG. 4.

The measured value, which has fulfilled the criteria, is shown blinking (in the example shown above it is tachycardia).

There will be a check box for the infection signs and symptoms listed,
  if the clinician support system received requested information through the second interface 107, wherein the delivered information meets the guideline criteria, and
  for all signs and symptoms which are not available through the second interface 107 or the information delivery tool 27.

The information delivery tool 27 is part of the clinician support system 1 as described before. The information delivery tool 27 sends requests to remote locations to provide the needed information, for example to collect the requested information from a connected central station or a connected remote medical laboratory center. If the requested information is not delivered by the information delivery tool 27, a window is triggered by the sepsis decision module 17 to trigger a manual input.

The clinician is requested to check a box whether the sign or symptom in question is both present and new, if so a confirmation is requested by the sepsis decision module 17. If the patient is mechanically ventilated, the Tachypnea box must be checked. If temperature or respiration rate is measured manually, the measured values can be delivered by using an "Enter RR" key (not shown) for respiration rate input and "Enter Temp" key (not shown) for manual temperature input. By selection of "Confirm" key 125 confirmation information is stored by the clinician support system 1, here by the sepsis decision module 17.

If a request window is closed without input, the request window will be triggered again after a predetermined period of time, especially after less than 15 min or 10 min or 5 min.

Further, the window will reappear, triggered by the sepsis decision module 17 if the HR, Temp or RR value, which previously fulfilled the criteria, now becomes worse, or after 8 hours, configurable to 12 hours, if at least one infection sign is still present.

Figure 5:
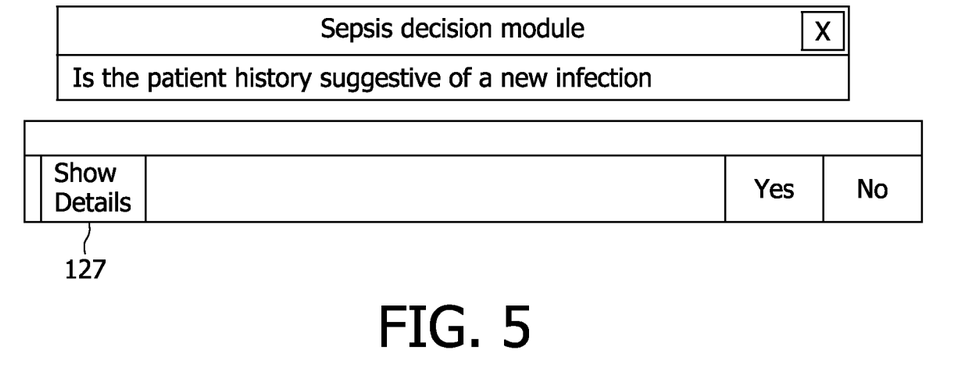
FIG. 5: New Infection window

If the sepsis decision module 17 recognized confirmation of two or more infection signs in the Infection Signs and Symptoms window of FIG. 4, a new pop-up window is triggered by the sepsis decision module 17 shown in FIG. 5, which window will appear on the display of the bedside patient monitor 101. In the following, all described windows are displayed on the display of the bedside patient monitor 101.

If the sepsis decision module 17 receives a signal representing that "Yes" is selected, the next screen is triggered by the sepsis decision module 17 requesting an input of a lactate measurement value.

If a signal representing the selection of "No" is received by the sepsis decision module 17, the decision phase will continue and the Infection Signs and Symptoms window, see FIG. 4, reappears if the measurement value which previously fulfilled the criteria becomes worse, or after 8 hours (configurable to 12 hours) at the latest if at least one infection sign is still present, which reappearance is triggered by the sepsis decision module.

Figure 6:
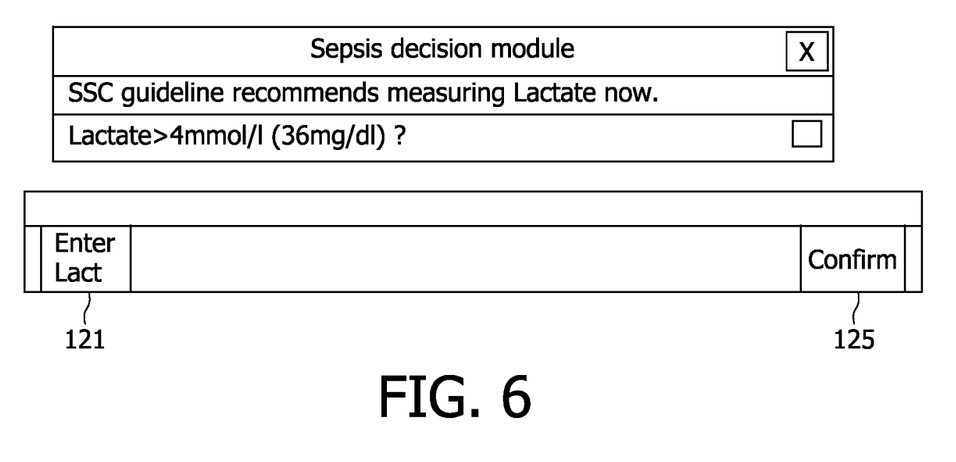
FIG. 6: Lactate request window

Manual lactate input, see FIG. 6:

The user is invited to manually enter the Lactate value, see FIG. 6, by selecting an "Enter Lact" key 121 if the lactate value is not provided to the sepsis decision module by the information delivery tool 27. If the information is delivered by the information delivery tool 27, the window of FIG. 5 does not appear. If the value entered is >4 mmol/l, the check box will be automatically checked.

By selecting "Confirm" 125 the entered value is sent to the sepsis decision module and the confirmation information is stored by the clinician support system. All information delivered during the use of the clinician support system 1 is stored in a storage, which is part of the bedside patient monitor. Additionally, storage of the provided information at a central storage of a connected central station can be made possible.

If a signal representing a Lactate value >4 mmol/l arrives at the sepsis decision module, the sepsis decision module 17 recognizes that the value meets the SSC guidelines criteria for sepsis. The sepsis decision module 17 triggers the display of a window to request approval by authorized clinician review. By a signal representing the authorized clinician review, the sepsis decision module is deactivated and the sepsis treatment module is activated. The signal representing authorized approval is generated by the manual input 105.

If a signal representing a Lactate value ≤4 mmol/l is delivered to sepsis decision module 17, a further window will appear, triggered by the sepsis decision module 17, in the case that the blood pressure value is not made available by the second interface 107 for continuous measurement. This window requests manual input of blood pressure values to determine on the basis of blood pressure values whether the patient meets the sepsis guideline criteria for sepsis.

Hypotension Evaluation

Figure 7:
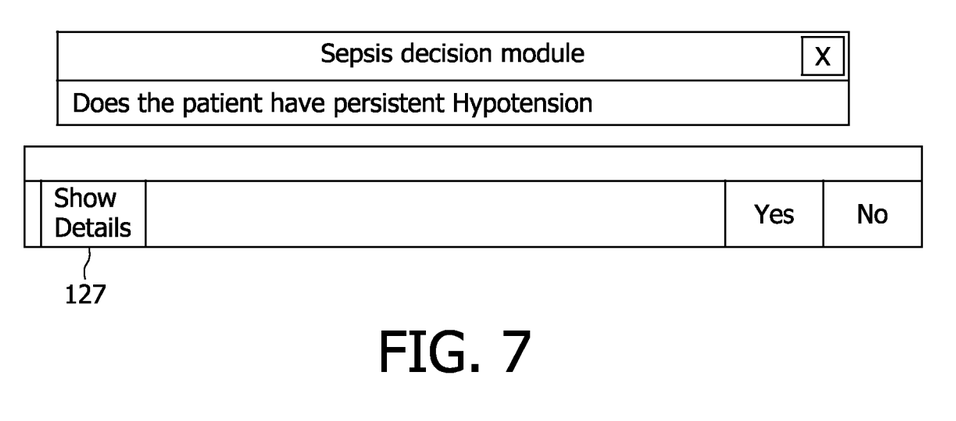
FIG. 7: Hypotension Evaluation request window

If the Lactate value was not above 4 mmol/l, the sepsis decision module 17 triggers the next window, see FIG. 7, to request the input in respect of persistent hypotension.

Hypotension is defined by the SSC guidelines as:
SBP <90 mmHg (12.0 kPa), or
MAP <65 mmHg (9.0 kPa), or
SBP decrease >40 mmHg (5.0 kPa) below baseline.

Figure 9:
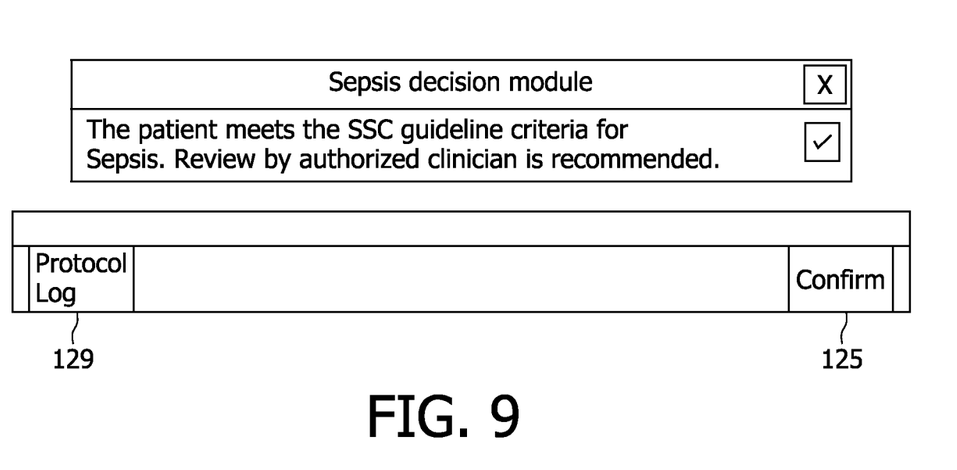
FIG. 9: Clinician authorized window

By selecting "Show Details" key 127, the definition of hypotension defined in the sepsis guidelines will be displayed. By selecting YES, persistent hypotension as defined in the sepsis guidelines is recognized by the sepsis decision module 17. Then a final window is triggered requesting authorized approval, by which authorized approval a signal is generated to deactivate the sepsis decision module 17 and to activate the sepsis treatment module 19, FIG. 9.

Figure 8:
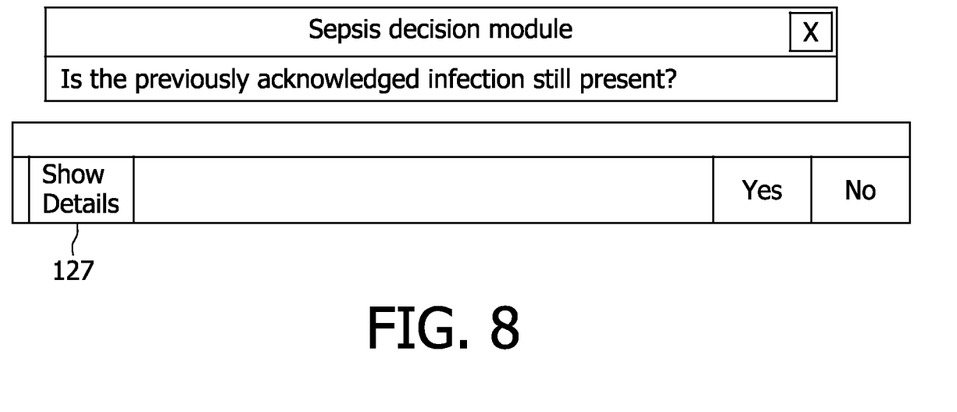
FIG. 8: Infection confirmation window

If a signal is generated representing the input that the patient does not have persistent hypotension, the sepsis decision module 17 triggers the appearance of the window shown in FIG. 8 after one hour. Information about the presence of a previously acknowledged infection is requested.

By inputting "Yes", the checks, see FIG. 6, FIG. 7, will be repeated. If "No" is selected, the decision support module 17 will continue—comparing heart rate, temperature and respiration rate values against the SSC criteria.

It is possible to review the process supported by the sepsis decision module by selection of button "Protocol Log" 129, which causes a display of the captured information to be triggered. It is possible to print out this documentation, see FIG. 14.

The sepsis treatment module 19 to support the clinician during the treatment process can be started by an authorized person only.

Sepsis Treatment Module

The clinician is supported to carry out the treatment of the patient in the recommended way proposed by SSC by using the sepsis treatment module 19. The treatment recommendations from SSC referred to as Sepsis Resuscitation Bundle (SRB) is presented in the display of the bedside patient monitor triggered by the sepsis treatment module 19, see FIG. 10. Further, the sepsis treatment module 19 monitors the implementation of the recommendations.

Figure 10:
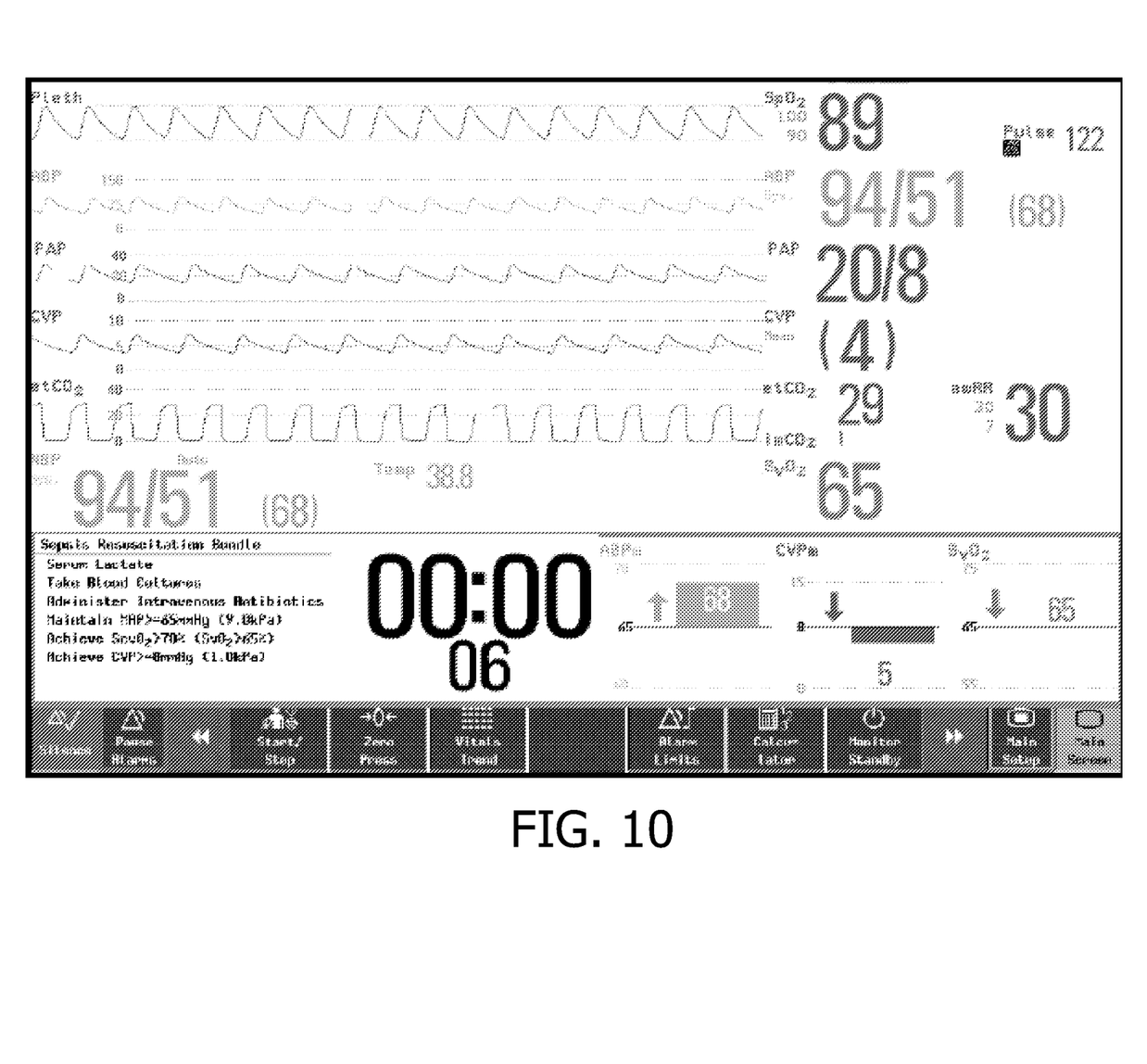
FIG. 10: Sepsis treatment screen

The sepsis treatment module 19 activates an indicator to show that the sepsis treatment module is activated. In this example the indicator is a yellow alarm displayed by the display of the bedside patient monitor.

The lower area of the display of the bedside patient monitor contains:
 a reminder list of the treatment recommendations
 a timer showing the time already passed in this phase
 three horizon trends for MAP, CVP and ScvO2 or SvO2, if these measured values are available.

If ScvO2 or SvO2 are not being continuously delivered through the second interface 107, a pop-up window will appear at hourly intervals to ask for a manually measured value triggered by the sepsis treatment module 19. When the window is closed without the requested information having been filled in, a pop-up window will appear after a predetermined time slice. The predetermined time slice is especially 10 or 15 minutes after the first pop up window appeared to request the required information.

The treatment process 6 according to the SRB supported by the sepsis treatment module 19 is monitored by the clinician support system. The status of all or one of the supported processes will be displayed on the display of the bedside patient monitor, if requested, using protocol log key 129. A standard clinician support window can be selected, so that the status of the running treatment module is displayed on the screen or display of the bedside patient monitor. If the clinician support window is not displayed, the display can be activated by user input. The clinician support system window 131 is displayed in the lower area of the patient monitor display. If the clinician support system window 131 is not displayed, the status of the running treatment modules, here at least status information about the running sepsis treatment process, appears on the display of the bedside patient monitor automatically once an hour, triggered by the sepsis treatment module 19.

Figure 11:
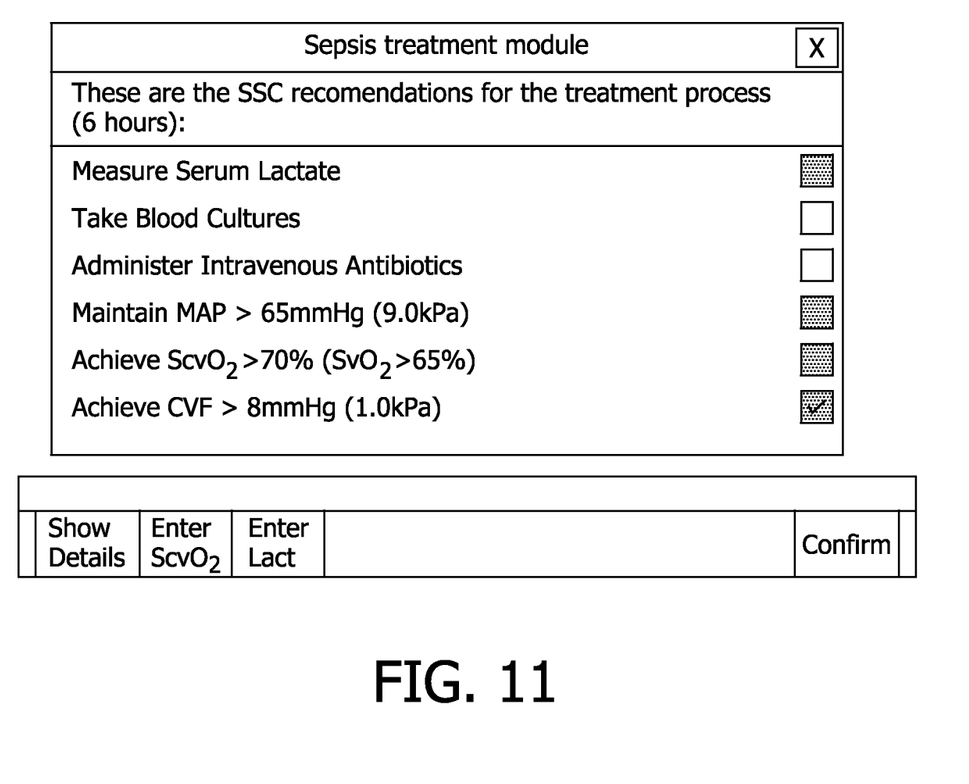
FIG. 11: Sepsis treatment recommendation monitoring window

In FIG. 11 the window for displaying the status of the treatment process of sepsis supported by the sepsis treatment module is shown. This window is displayed on the screen of the bedside patient monitor. The window content is in conformity with the treatment guidelines proposed by the SSC.

By selection of "Enter Lact" key or button 121, the process of manual information input of the lactate value is supported and the information will be stored by the clinician support system. When the lactate value is entered, or if a lactate value has previously been entered or delivered by the information deliver tool 27, the box will be checked.

Further, the clinician is supported by the registration of blood cultures that were taken. The information of these blood cultures can be delivered to the sepsis treatment module by manual input. The information expected from the registered blood cultures can be requested automatically after a predetermined time slice by the information delivery tool. By checking the "Administer Intravenous Antibiotics" box the clinician is supported in noting the starting time of broad spectrum antibiotic therapy in a convenient way.

The remaining three recommendations of the SSC treatment guideline will be automatically compared to the available information by the sepsis treatment module 19. Therefore, the signals available through the second interface 107 will be checked. A box will be checked when the sepsis treatment module has recognized that the recommendation has been fulfilled.

If the ScvO2 value is manually measured, the value can be entered in a convenient way by using the "Enter ScvO2" key 123. The box will be checked automatically on whether the value fulfils the recommendation.

In the case that MAP ScO2/SvO2 values are not automatically delivered to the sepsis treatment module 19 by the second interface for continuous measurement and neither by the information delivery tool 27, the sepsis treatment module 19 provides the possibility for manual input, which is possible, at the earliest, when the timer indicates that 4 hours have lapsed since the activation of the sepsis treatment module 19 to ensure that these values are maintained halfway through treatment. The boxes are checked on whether if the recommendation has been fulfilled.

More details of the recommendations are displayed on the screen of the bedside monitor by choosing "show details"

key 127. This information is stored in the clinician support system storage 31 supporting sepsis. The bedside patient monitor comprises a confirm button. The sepsis treatment module 19 recognizes the activation of the confirm button by an authorized person. Thus it is stored that the check boxes reflect the current treatment status.

During the sepsis treatment phase an overview window displaying the sepsis treatment status and enabling entries to be made can be opened, see FIG. 11. The recommendations will be shown as follows:

Recommendations, which are not yet fulfilled, are shown in black. They also appear in the list in the lower area of the clinician support system screen.

Recommendations of the SSC guidelines which are overdue, are shown in red.

In the lower area of the clinician support system screen, all recommendations are displayed. The recommendations that have been carried out are shown in gray.

Ending Sepsis Treatment Module

Figure 12:
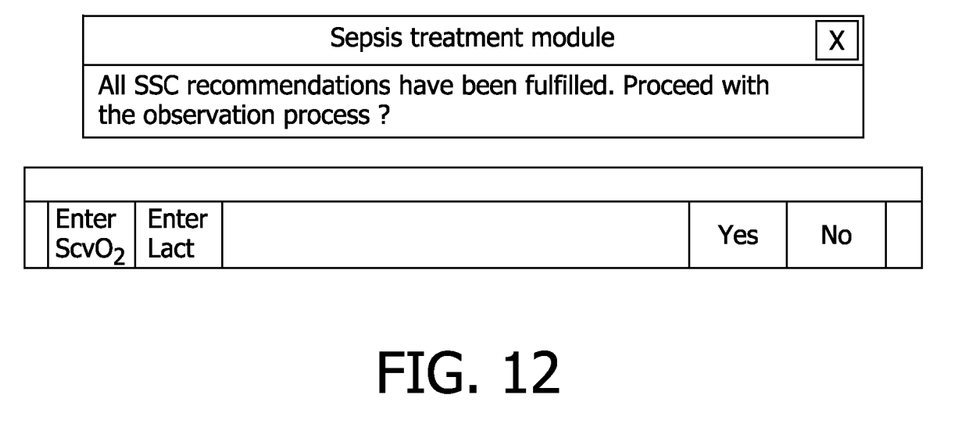
FIG. 12: Sepsis treatment deactivation window

When all recommendations have been fulfilled and confirmed, or when 6 hours have passed since the treatment module was started, the sepsis treatment module 19 is deactivated. A window is generated by the clinician support system 1 to trigger the clinician to generate a confirmation signal to start the sepsis observation module 21. By pressing the "NO" key a signal is generated to trigger an extension in the active state by 1 hour of the sepsis treatment module 19.

Sepsis Observation Module

After deactivation of the sepsis treatment module the clinician is supported in the observation of the patient's status by the sepsis observation module. The SSC has generated a guideline to observe the status of the patient after finishing the sepsis treatment of the patient. The guideline is named Sepsis Management Bundle (SMB). The parameters of the observation guideline supported by the sepsis observation module 21 are presented and the implementation of the recommendations is monitored. When the sepsis observation phase begins, the clinician support system screen 131 will automatically appear on the monitor (if configured and available on the monitor). In the lower area of the display, the list of recommendations for the observation phase will replace the list for the treatment phase. The timer shows the combined time for the treatment and the observation phases.

Monitoring the Sepsis Management Bundle Recommendations

Figure 13:
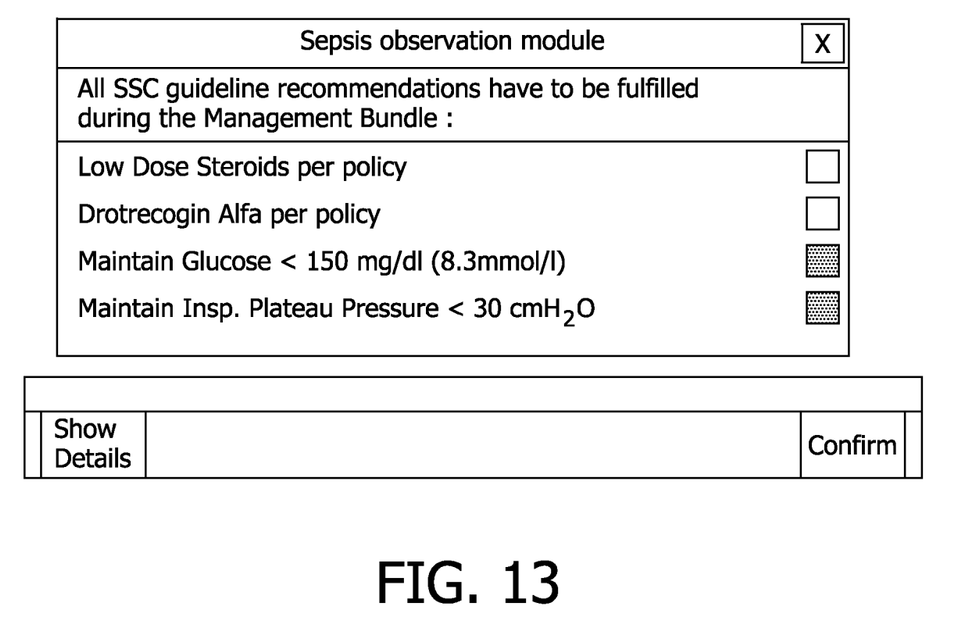
FIG. 13: Sepsis observation window

By the selection of the lower area of the clinician support system screen, a signal is generated to trigger the appearance of the sepsis observation window, see FIG. 13. In the case that the observation is not triggered by manual input, the sepsis observation window will appear automatically once every six hours, triggered by the sepsis observation module 21, see FIG. 13.

This window supports the clinician to check the "Low Dose Steroids" recommendation and/or the "Drotrecognin Alfa" recommendation. These parameters may not be requested if the sepsis observation module 21 or observation support module has been configured not to do so in the actual hospital. The clinician is requested to check the "Low Dose Steroids per policy" box at the time of starting steroid therapy.

The clinician is requested to check the "Drotrecogin Alfa per policy" box at the time of starting recombinant human activated protein C therapy.

The clinician is requested by the window shown in FIG. 13 to check the boxes "Glucose" and "Inspiratory Plateau Pressure" when the timer has reached 20 hours to ensure that long-term stabilization of these values is achieved. These boxes should be checked if the recommendations are fulfilled.

By pressing the details button 127 on the screen, a window containing more details about the recommendations will be opened. The recommendations are stored in the sepsis observation module 21. Therefore, the clinician support system comprises a storage 31, which is part of the bedside patient monitor.

The stored recommendations can be updated from time to time via the internet or the planned maintenance service.

By pressing the confirm button 125 on the sepsis observation screen, a signal is generated assigned to the actual treatment status reflected by the checked boxes.

Ending Sepsis Observation Phase

The sepsis observation phase support provided by the sepsis observation module 21 normally ends 24 hours after the sepsis treatment module 19 is started, as documented by the clinician support system timer on the clinician support system screen.

The clinician will be asked to confirm with the "Yes" key that normal monitoring should now begin. By selecting "No", the sepsis observation phase supported by the sepsis observation module 21 is extended by a further 6 hours.

After completion of active observation, and a sepsis standby phase supported by the sepsis observation module begins. The sepsis standby phase allows time for further patient stabilization and recovery. During this phase, the sepsis decision module 17 is suspended. The standby phase is by default 7 days but can be adjusted in the configuration mode of the sepsis observation module 21.

Figure 14:
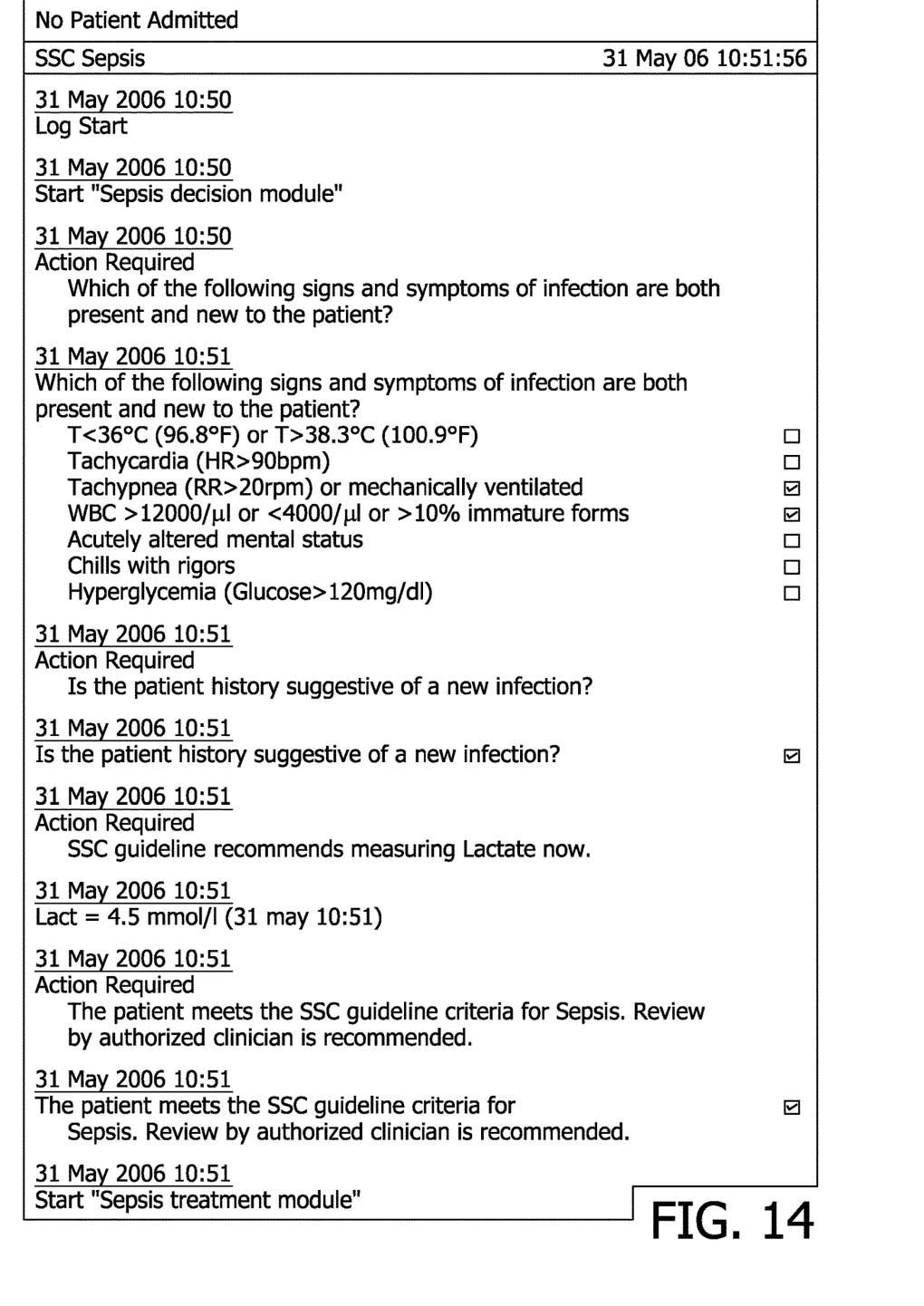

In the storage 31 all user interactions, alarms and phase transitions of one disease-specified support are stored. So all user interactions and alarms and phase transitions during the sepsis treatment supported by the sepsis decision, sepsis treatment and sepsis observation module are stored. The user can request to display this stored information on the display of the bedside patient monitor by pressing the protocol log key 129, and by pressing a print button, this information is printed on a connected printer. The displayed overview can be restricted, or not, to one disease. So disease-specific overview sheets can be generated by the clinician support system 1. A sepsis related overview generated by the clinician support system 1 is shown in FIG. 14. This storage contents is cleared whenever the patient assigned to the bedside monitor is discharged.

It is essential that patients are discharged when monitoring ends. As a reminder, the clinician support system 1 generates a pop-up window when the monitor has been switched off or is in standby mode, or is not monitoring basic vitals for a predetermined time, especially more than 6, or 12 hours. This window supports the clinician to discharge a patient by asking whether a new patient is being monitored, and offers a pop-up key to discharge the previous patient if this is the case.

The process of the sepsis decision, sepsis treatment and sepsis observation procedure described before is stored in a history file, which could be displayed and printed. The history file could be used to figure out which person has made for an example a manual entry or checked off recommendations, see FIG. 14.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

REFERENCE NUMERALS 1. clinician support system
3. decision support module
4. decision process
5. treatment support module
6. treatment process
7. observation support module
8. observation process
11. disease-specified decision module
13. disease-specified treatment module
15. disease-specified observation module
17. sepsis decision module
19. sepsis treatment module
21. sepsis observation module
23. weaning treatment module
25. weaning observation module
27. information delivery tool
29. network connection
31. local storage
101. bedside patient monitor
103. display/screen
105. first interface—for manual patient-related input
107. second interface—automated sensor signal input
109. sensor
115. network connection
119. central station
121. Lact key
123. ScvO2 key
125. confirm key
127. details key
131. clinician support window

The invention claimed is:

1. A bedside patient monitor comprising:
a clinician support system,
a first interface including an input configured to manually input medical information related to a patient associated with the bedside monitor and a display configured to continuously display physiological values of the patient;
a second interface configured to continuously input sensor signals from sensors configured to continuously measure the physiological values of the patient;
wherein the clinician support system comprises:
at least one disease-specific treatment module which supports the clinician in a treatment process, the disease-specific treatment module being started only by a manual input by a qualified clinician to the first interface, wherein the manual input includes a fingerprint and the disease-specific treatment module uses the fingerprint to verify that a person inputting the manual input is authorized to start the disease-specific treatment module;
at least one disease-specific observation support module configured for observation of the continuously measured physiological values of the patient, the disease-specific observation module being activated by a signal generated through deactivation of the disease-specific treatment module;
wherein the disease-specific treatment module is deactivated in response to the manual input by the qualified clinician confirming that the disease-specific treatment module is to be deactivated and the disease-specific observation support module started to observe the continuously measured physiological values of the patient; and,
wherein the disease-specific observation support module is configured to:
in response to the deactivation of the disease-specific treatment module, display a list of observation recommendations of the specified disease on the first interface display.

2. The bedside patient monitor as claimed in claim 1, wherein the clinical support system further includes:
a disease-specific decision module which is configured to compare the sensor signals and a manual patient-related input with disease-specific detection guidelines to detect early signs and symptoms of a specified disease and in response to detecting the early signs and symptoms, generating a display on the first interface display indicating the presence of the signs and symptoms of the specified disease.

3. The bedside patient monitor as claimed in claim 2, comprising an indicator for signaling that the disease-specific treatment module is running.

4. The bedside patient monitor as claimed in claim 2, wherein the clinician support system comprises an information delivery tool to deliver requested information requested by at least one of the disease-specific modules, wherein the information delivery tool generates a pop-up window to trigger the manual patient-related input through the first interface if the requested information is not available through the interface for automatic input or connected remote sources.

5. The bedside patient monitor as claimed in claim 4, wherein the remote resource is a remote central station or remote microanalysis center.

6. A method of clinician support comprising, with a patient-specific bedside monitor:
automatically and continuously inputting sensor signals from patient physiological sensors into the bedside monitor;
manually inputting patient-specific information that is not available from the sensor signals on a first interface of the bedside monitor;
with at least one disease-specific decision module of a plurality of disease-specific decision modules of the bedside monitor, analyzing the sensor signals and the patient-related information for signs and symptoms of a presence of a specific disease;
displaying the signs and symptoms on the first interface of the bedside monitor;
requesting additional patient related information for the analyzing by the disease-specific decision module through the first interface of the bedside monitor;
starting a disease-specific treatment module of the bedside monitor with a manual input from a qualified clinician to the first interface of the bedside monitor;
with the disease-specific treatment module of the bedside monitor, controlling the first interface of the bedside monitor to display a list of disease-specific treatment step recommendations;
displaying a completion status of the recommended treatment steps on the first interface of the bedside monitor;
deactivating the disease-specific treatment module of the bedside monitor;
activating an observation support module by a signal generated through the deactivation of the disease-specific treatment module;

with the observation support module of the bedside monitor, controlling the first interface of the bedside monitor to display a list of observation recommendations; and
running each of the plurality of disease-specific decision modules of the bedside monitor of different specific diseases in parallel, and running only one disease-specific treatment module at the same time as the plurality of disease-specific decision modules perform monitoring of the different specific diseases.

7. The method of clinician support as claimed in claim 6, wherein starting the disease-specific treatment module of the bedside monitor includes verifying that a clinician inputting the manual input on the first interface of the bedside monitor is qualified to start the disease-specific decision module.

8. The method of clinician support as claimed in claim 6, wherein the manual inputting of the patient-specific information on the first interface of the bedside monitor requested by the disease-specific decision module of the bedside monitor is executed before manually inputting patient-specific information on the first interface of the bedside monitor requested by the disease-specific observation module of the bedside monitor.

9. The method of clinician support as claimed in claim 6, wherein an unanswered manual information request is displayed on the first interface of the bedside monitor again after a predetermined time.

10. The method as claimed in claim 6, wherein the list of disease-specific treatment steps is displayed on the first interface of the bedside monitor and further including with the first interface receiving confirmations confirming that each of the listed disease-specific treatment recommendations have been fulfilled and wherein the disease-specific treatment module of the bedside monitor deactivated and the observation support module of the bedside monitor is activated in response to receiving on the first interface of the bedside monitor confirmations that all of the listed disease-specific recommendations have been fulfilled.

11. The bedside patient monitor as claimed in claim 2, wherein the disease-specific treatment model is configured to:
in response to the manual input on the first interface of the bedside monitor, display a list of treatment process recommendations for the specific disease on the first interface of the bedside monitor;
receive manual inputs on the first interface of the bedside monitor indicating that each treatment process on the list has been fulfilled;
display a status of the treatment process on the first interface of the bedside monitor.

12. The method as claimed in claim 10, wherein the sensor signals are indicative of vital signs of a patient disposed in a bed adjacent the bedside monitor and wherein the disease-specific decision module analyzes the sensor signals and the patient-related information for signs or symptoms of sepsis in the patient disposed in the bed adjacent the bedside monitor, if the disease-specific decision module detects sepsis in the patient disposed in the bed adjacent the bedside monitor, the disease-specific treatment module displays a list of sepsis treatment recommendations for the patient disposed in the bed adjacent the bedside monitor.

13. A bedside patient monitor for monitoring a patient in an adjacent bed, comprising:
a first interface configured to receive manual patient-related inputs;
a second interface configured to receive continuous input of sensor signals indicative of physiological values of the patient, a display screen,
one or more processors configured to:
compare the sensor signals and the manual patient-related input with disease-specific detection guidelines to detect early signs and symptoms of a specified disease and in response to detecting the early signs and symptoms, generating a display in a window on the display screen indicating the presence of the signs and symptoms of the specified disease;
in response to receiving a manual input indicating treatment is to be commenced from the first interface and an identification code or fingerprint to verify that a person inputting the manual input is authorized to start the disease-specific treatment, displaying treatment recommendations in a treatment window on the display screen;
in response to receiving input from the first interface that the treatment recommendations have been completed and a confirming input by a qualified clinician, closing the treatment window;
after closing the treatment window, displaying a list of observation recommendations of the specified disease in an observations window of the display screen;
in response to the manual input on the first interface of the bedside monitor, display a list of recommendations of treatment processes for the specific disease on the first interface of the bedside monitor;
receive manual inputs on the first interface of the bedside monitor indicating that each of the treatment processes on the list has been fulfilled; and
display a status of the fulfilling of the treatment processes on the list on the first interface of the bedside monitor.

14. A bedside patient monitor comprising:
a first interface including a display and a manual input device;
a second interface configured to receive a continuous input of sensor signals carrying physiological information from sensors mounted to a patient, at least some of the physiological information being displayed on the first interface display;
a sepsis treatment module which is activated by a manual input from a qualified clinician on the manual input device, the sepsis treatment module being triggered by the manual input to display on the first interface display a list of recommended treatments which are configured to be checked off by inputs on the first interface manual input as the treatments are implemented;
a sepsis observation module which is activated by deactivation of the sepsis treatment module, the sepsis observation module causing the first interface display to display an observation guideline including a list of parameters to be observed or measured, the list being displayed for a preselected duration which duration is extendible by manual inputs on the manual input device;
wherein the sepsis treatment model is configured to:
in response to the manual input on the first interface of the bedside monitor, display a list of recommendations of treatment processes for the specific disease on the first interface of the bedside monitor;
receive manual inputs on the first interface of the bedside monitor indicating that each of the treatment processes on the list has been fulfilled; and display a status of the fulfilling of the treatment processes on the list on the first interface of the bedside monitor.

15. The bedside patient monitor as claimed in claim 14, further including:
a sepsis decision module which receives the physiological information from the sensors via the second interface, causes the first interface display to display requests for additional physiological information, and receives the additional physiological information from the manual input device, the sepsis decision module screening the physiological information from the sensors and the additional information for signs and symptoms of sepsis.

16. The bedside patient monitor as claimed in claim 15, wherein the sepsis decision module controls the first interface display to display a list of signs and symptoms of sepsis.

17. The bedside patient monitor as claimed in claim 15, further including:
an information delivery tool which requests information from remote patient or laboratory information storage stations.

18. The bedside patient monitor as claimed in claim 14, wherein the bedside monitor is configured to be disposed adjacent a patient bed on which the patient to whom the sensors are mounted is disposed;
wherein the physiological information includes heart rate, respiration rate, and temperature; and
a sepsis decision module configured to continuously receive the heart rate, respiration rate, and temperature of the patient and compare the received heart rate, respiration rate, and temperature with sepsis criteria, and in response to the received heart rate, respiration rate, and temperature meeting the sepsis criteria, causing a pop-up window to appear on the first interface display.

* * * * *